US010952911B2

(12) United States Patent
Kurihara et al.

(10) Patent No.: US 10,952,911 B2
(45) Date of Patent: Mar. 23, 2021

(54) INCONTINENCE ABSORBENT ARTICLE WITH COTTON FIBER FRONT-SURFACE SHEET

(71) Applicant: DAIO PAPER CORPORATION, Ehime (JP)

(72) Inventors: Ryoko Kurihara, Tochigi (JP); Mariko Nagashima, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 314 days.

(21) Appl. No.: 15/778,484

(22) PCT Filed: Nov. 30, 2016

(86) PCT No.: PCT/JP2016/085500
§ 371 (c)(1),
(2) Date: May 23, 2018

(87) PCT Pub. No.: WO2017/094756
PCT Pub. Date: Jun. 8, 2017

(65) Prior Publication Data
US 2018/0344539 A1 Dec. 6, 2018

(30) Foreign Application Priority Data

Nov. 30, 2015 (JP) .............................. JP2015-234220

(51) Int. Cl.
*A61F 13/511* (2006.01)
*A61F 13/512* (2006.01)
(Continued)

(52) U.S. Cl.
CPC ........ *A61F 13/51121* (2013.01); *A61F 13/47* (2013.01); *A61F 13/511* (2013.01);
(Continued)

(58) Field of Classification Search
CPC .. A61F 13/47; A61F 13/511; A61F 13/51121; A61F 13/512; A61F 2013/5104; A61F 2013/530007; B29D 11/00865
See application file for complete search history.

(56) References Cited

U.S. PATENT DOCUMENTS 5,821,179 A * 10/1998 Masaki ............. A61F 13/15203
442/375
6,153,209 A * 11/2000 Vega ....................... A61L 15/34
424/404
(Continued)

FOREIGN PATENT DOCUMENTS

EP    1 688 522    * 8/2006 ............... D04H 1/46

*Primary Examiner* — Michele M Kidwell
(74) *Attorney, Agent, or Firm* — Wenderoth, Lind & Ponack, L.L.P.

(57) ABSTRACT

To provide an absorbent article that uses a cotton fiber in a front-surface sheet, prevents rebounding, improves an absorption speed, and reduces a diffusion range of urine in the front-surface sheet. An incontinence pad 1 having a medium or larger volume that absorbs 20 cc or a larger volume of urine is provided. A front-surface sheet 3 is a spunlace nonwoven fabric made of 100% cotton fiber by weight, is coated with a water repellent agent and has many front-face/back-face penetrating openings 10 in a region containing a part corresponding to an excreting hole. The absorber is made of a pulp fiber that does not contain synthetic fiber and a superabsorbent polymer, a basis weight of the pulp fiber being 75 to 300 g/m², a basis weight of the superabsorbent polymer being 85 to 185 g/m², and a ratio of the pulp fiber and the superabsorbent polymer being pulp fiber:superabsorbent polymer=70 to 30% by weight:30 to 70% by weight.

4 Claims, 4 Drawing Sheets

(51) Int. Cl.
*A61F 13/47* (2006.01)
*A61F 13/51* (2006.01)
*A61F 13/53* (2006.01)

(52) U.S. Cl.
CPC .... *A61F 13/512* (2013.01); *A61F 2013/5104* (2013.01); *A61F 2013/530007* (2013.01)

(56) References Cited

U.S. PATENT DOCUMENTS

2008/0262459 A1* 10/2008 Kamoto ................ A61F 13/534
 604/375
2016/0222563 A1* 8/2016 Sheehan .................. D04H 1/49

* cited by examiner

[Fig. 1]
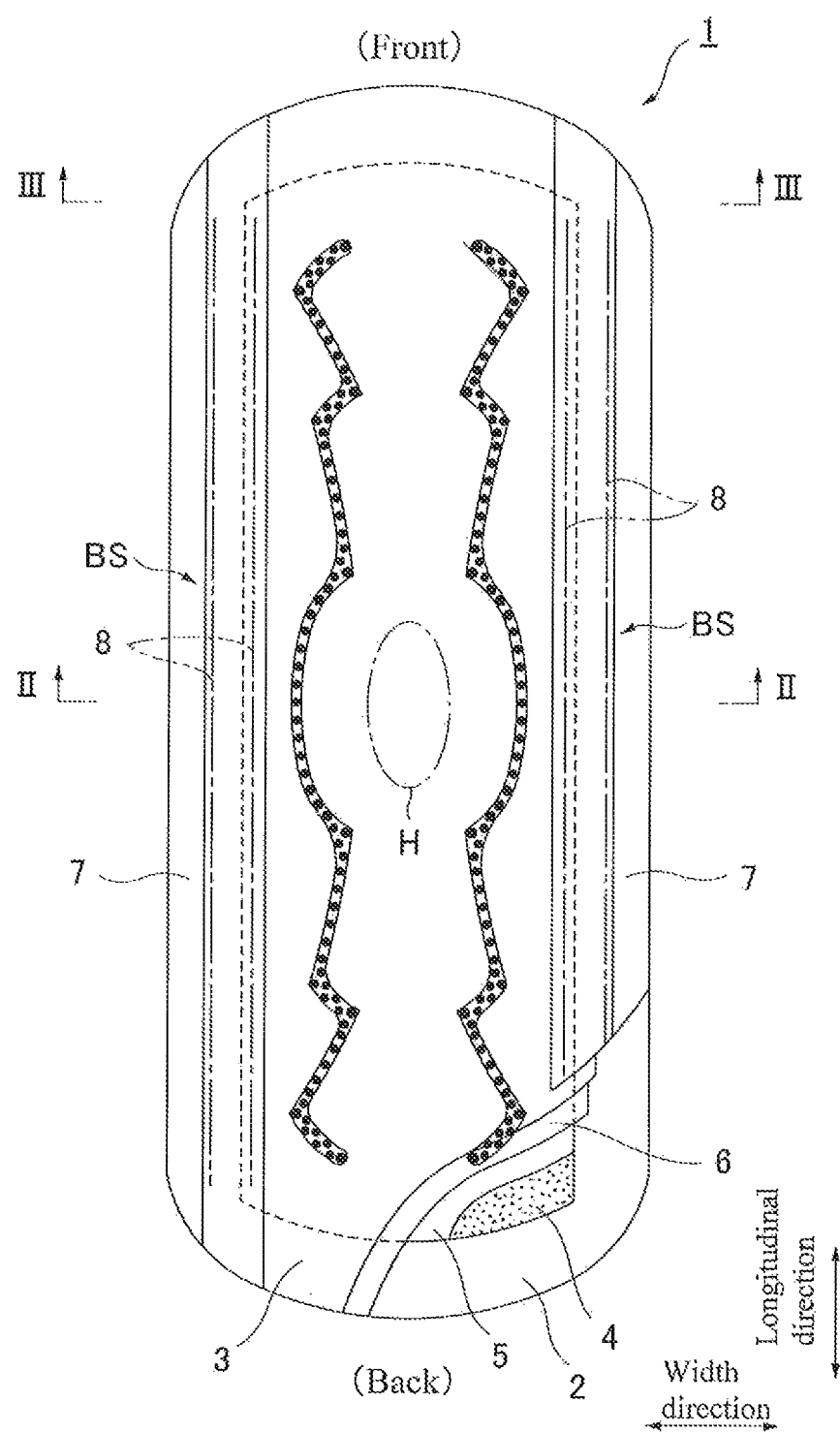

[Fig. 2]
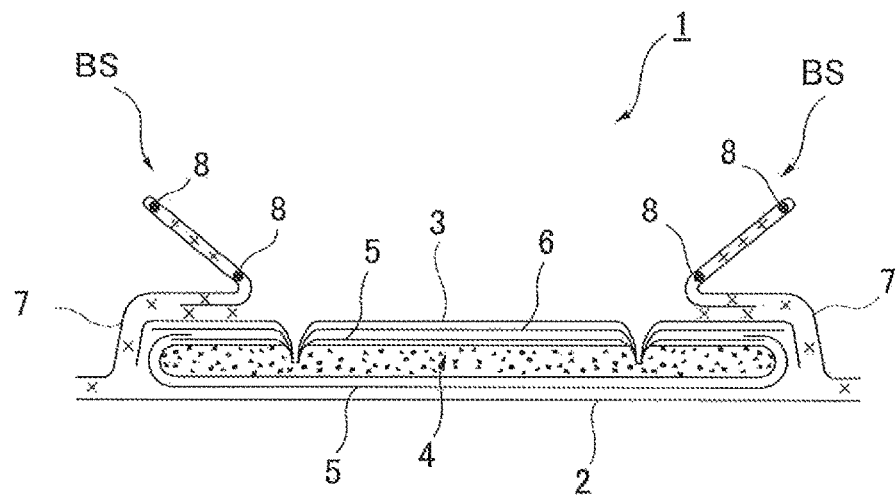
[Fig. 3]
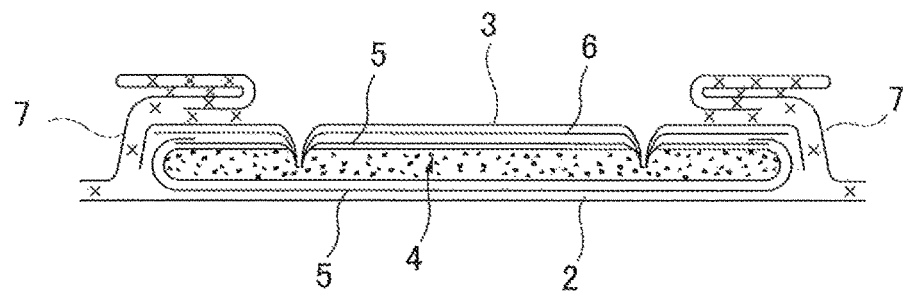

[Fig. 4]
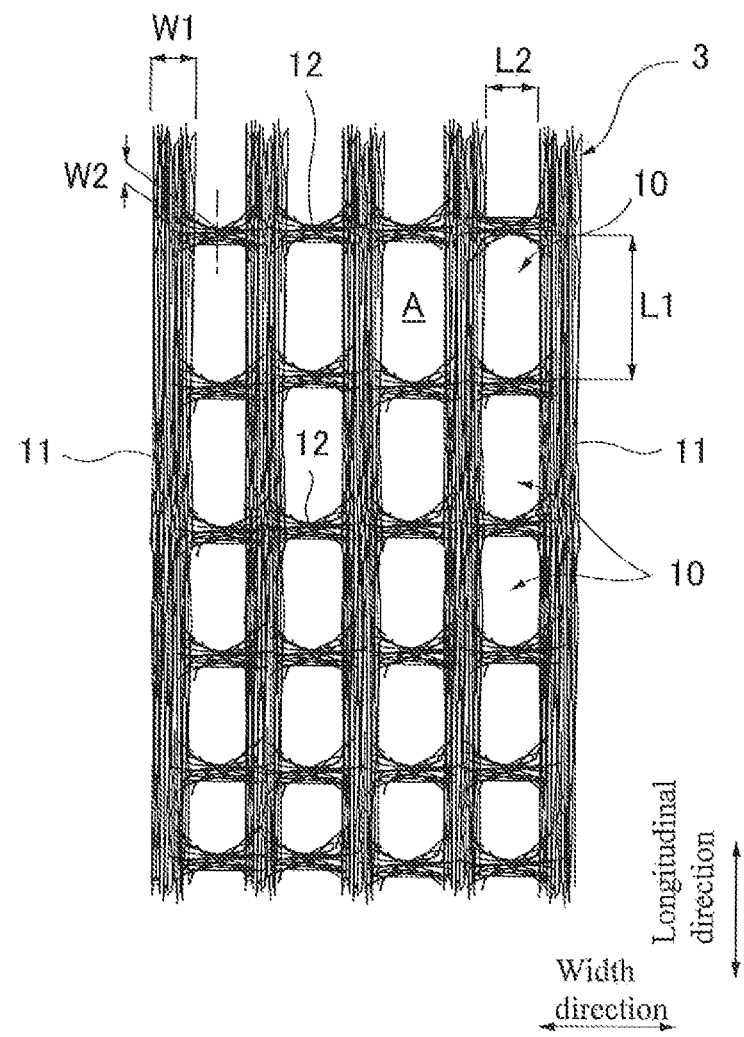

[Fig. 5]
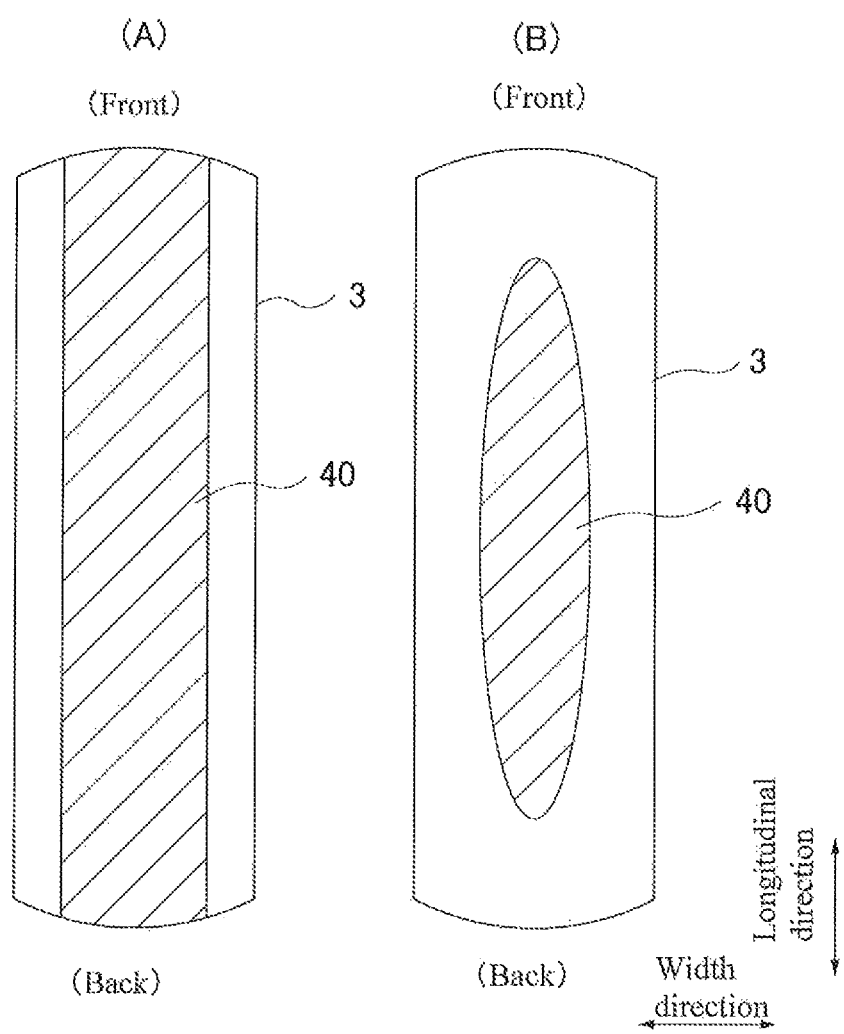

INCONTINENCE ABSORBENT ARTICLE WITH COTTON FIBER FRONT-SURFACE SHEET

TECHNICAL FIELD

The present invention relates to an absorbent article that is mainly used for incontinence pads, and in particular, relates to incontinence pads of medium or larger capacity that absorb a total volume of urine that is 20 cc or larger.

BACKGROUND ART

Conventionally, as absorbent articles for women such as incontinence pads, vaginal discharge sheets, panty liners, and sanitary napkins, ones in which an absorber made of paper cotton such as pulverized pulp or the like is interposed between an impermeable back-surface sheet such as a polyethylene sheet or a polyethylene sheet-laminated nonwoven fabric and a front-surface sheet are known.

The front-surface sheet forms a skin-contact surface and is required to be soft, to be able to obtain a dry feeling on skin even after absorption of an excreted liquid, to have little irritation to skin or the like. As materials that satisfy such requirements, nonwoven fabrics of synthetic fibers and resinous mesh sheets are broadly adopted in the field of absorbent articles, particularly in the field of incontinence pads. However, there was a problem that the front-surface sheet made of the synthetic fiber causes itchiness, irritation or the like.

In order to solve this problem, a front-surface sheet having cotton fiber as a raw material has been proposed. However, in the absorbent articles, while the front-surface sheet is desired to have high liquid permeability and to make the liquid speedily reach the absorber, when regular degreased cotton fiber was contained in the front-surface sheet, there was a problem that the front-surface sheet itself has high liquid retentiveness and is likely to leave a sticky feeling on a surface.

Furthermore, an absorbent article having a front-surface sheet made of cotton fiber has an advantage that can realize a soft feeling on the skin like underwear, however, when a large volume of body fluid is excreted, since the liquid retentiveness is high as described above, the body fluid remains in the front-surface sheet, and when wearing the absorbent article for a long time, a moist feeling or irritation may be caused. Therefore, in the conventional absorbent articles, when the cotton fiber is used in the front-surface sheet, its use was limited to products such as vaginal discharge sheets in which an absorption volume of the body fluid is slight.

As absorbent articles that use such a cotton fiber in the front-surface sheet, the following Patent Document 1 can be given as an example. In Patent Document 1 below, an absorbent article that includes a top sheet made of spunlace nonwoven fabric which is made of 40 to 100% cotton fiber by weight and 60 to 0% synthetic fiber by weight and which is coated with a water repellent agent, the top sheet having water absorbency of a skin-contact surface of 0 mm to 5 mm, and including many front-face/back-face penetrating openings in at least an excreting hole part is disclosed. According to the absorbent article such as this, due to adoption of the spunlace nonwoven fabric having high cotton fiber content as the top sheet, many advantages of the cotton fiber such as excellent skin contact and difficulty in causing itchiness or irritation can be obtained. Furthermore, residual liquid on a surface that becomes a problem at this time is sufficiently improved by securing water absorbency of the skin-contact surface at a sufficiently low level due to the coating (external addition) of the water repellent agent. However, if the water absorbency is only made low, a liquid part of the excreted matter cannot easily permeate through the top sheet, which causes lateral leakage or the like; hence, in the absorbent article described in Patent Document 1, many front-face/back-face penetrating openings are provided in at least the excreting hole part in the top sheet to make it possible to speedily absorb the liquid. As a result thereof, in Patent Document 1, advantages such as that the sticky feeling due to residual liquid on a surface may be sufficiently prevented, and that excreted liquid that has been absorbed cannot easily return to a front-surface side of the top sheet due to the water repellency of the top sheet, are described.

PRIOR ART DOCUMENTS

Patent Document 1: JP 2010-269029 A

SUMMARY OF THE INVENTION

Problem to be Solved by the Invention

Although in the absorbent article described in Patent Document 1, attempt has been made to reduce the liquid retentiveness in the front-surface sheet by improving the water repellency or permeability of the front-surface sheet, however, depending on a property of the absorber, when a content of a superabsorbent polymer is excessively low, due to low liquid retentiveness of the absorber, a rebound occurred in some cases. When the cotton fiber is used in the front-surface sheet, rebounded urine tends to remain on a surface; furthermore there was a concern of strengthening the sticky feeling.

Contrary to this, when the content ratio of the superabsorbent polymer is excessively large, an initial absorption speed of the absorber becomes slow, whereby, in a case where urine is instantaneously excreted by force applied to an abdominal part such as when sneezing, coughing, or when holding a heavy object, the absorption speed of the absorber at the initial stage of absorption is insufficient, which causes rebounding to the surface, and thus it was difficult to obtain a dry feeling immediately after urination.

Furthermore, in the case where the cotton fiber is used in the front-surface sheet, when the absorption speed of the absorber is slow, even when the water repellent agent is coated, there was concern that the residual liquid tends to remain on the front-surface sheet and diffusion on the front-surface sheet proceeds, causing expansion of a diffusion range of urine.

In light of the above, a primary object of the present invention is to provide an absorbent article using cotton fiber on the front-surface sheet in which rebounding is prevented, the absorption speed is improved, and the diffusion range of urine in the front-surface sheet is reduced, by providing in the absorbent article an absorber in which predetermined amounts of pulp and polymer are blended.

Means for Solving the Problem

As the present invention according to claim 1 for solving the above problem, in an absorbent article in which an absorber is interposed between a front-surface sheet and a back-surface sheet, an absorbent article is provided, characterized in that:

the absorbent article is an incontinence pad having a medium or larger volume that absorbs 20 cc or a larger volume of urine;

the front-surface sheet is a spunlace nonwoven fabric made of 100% cotton fiber by weight, is coated with a water repellent agent and has many front-face/back-face penetrating openings in a region containing a part corresponding to an excreting hole; and the absorber is made of a pulp fiber that does not contain synthetic fiber and a superabsorbent polymer, a basis weight of the pulp fiber being 75 to 300 g/m$^2$, a basis weight of the superabsorbent polymer being 85 to 185 g/m$^2$, and a ratio of the pulp fiber and the superabsorbent polymer being pulp fiber:superabsorbent polymer=70 to 30% by weight:30 to 70% by weight.

The invention according to Claim 1 above targets an incontinence pad that absorbs urine excreted instantaneously when force is applied to an abdominal part at the time of such as when sneezing, coughing, or when holding a heavy object, that has a medium or larger volume and that absorbs a total volume of 20 cc or larger. In many cases, the incontinence pad is continuously used until two instances of incontinence, that is, it is frequently worn for a long time in a state of after the first incontinence, and after urination again, it is disposed. Accordingly, in the incontinence pad having a medium or larger volume such as this, a function of instantaneously absorbing and retaining a predetermined amount of urine and of maintaining a dry feeling on a surface is required.

Furthermore, in the incontinence pad of medium or larger volume which targets incontinence occurring when a force is applied to an abdominal part, when such conditions are not satisfied, the urination does not occur, in many cases, the incontinence pad is worn for a long time. Therefore, as the present absorbent article, an absorbent article that includes the front-surface sheet that is made of a spunlace nonwoven fabric made of 100% cotton fiber by weight coated with a water repellent agent and that has many front-face/back-face penetrating openings in a region containing a part corresponding to an excreting hole is used. Therefore, due to adoption of the spunlace nonwoven fabric made of 100% cotton fiber by weight, a soft feeling on the skin is obtained, and skin trouble during wearing such as itchiness or irritation is made to occur less easily even when wearing for a long time. The residual liquid on a surface that becomes a problem at this time may be sufficiently improved by coating with the water repellent agent. Furthermore, since many front-face/back-face penetrating openings are provided in a region of the front-surface sheet containing a part corresponding to an excreting hole, the body fluid permeates speedily. When a formation region of the openings is formed not so as to contain a part corresponding to the excreting hole, a situation where the incontinence region cannot be covered occurs, urine remains in the front-surface sheet to cause a sticky feeling, and skin trouble such as itchiness or irritation tends to occur during wearing.

Furthermore, in the present absorbent article, by using an absorber in which a pulp fiber and a superabsorbent polymer each is constituted at a predetermined basis weight and the pulp fiber and the superabsorbent polymer each is constituted at a predetermined weight ratio, even when the urine is instantaneously excreted, by making the pulp fiber having a rapid absorption speed rapidly absorb urine immediately after the urination, thereafter, the body fluid absorbed by the pulp fiber is gradually absorbed by the superabsorbent polymer and retained therein, thereby, the rebounding to the surface is prevented. Furthermore, since the urine is securely absorbed and retained in the absorber from immediately after the urination and the residual liquid on the front-surface sheet becomes slight, the diffusion range of the urine in the front-surface sheet can be reduced.

Although it is well-known to constitute the absorber with the pulp fiber and the superabsorbent polymer, in particular, like in the present invention, under the conditions where the front-surface sheet is formed of the spunlace nonwoven fabric that is made of 100% cotton fiber by weight, is coated with the water repellent agent and has many front-face/back-face penetrating openings formed in a region containing a part corresponding to the excreting hole, it is considered that the optimum ranges of an amount of the pulp fiber, an amount of the superabsorbent polymer and a blending ratio thereof are different from the case where a nonwoven fabric or a mesh sheet made of an olefin-based resin such as polyethylene or polypropylene is used as the front-surface sheet.

In general, in a water absorption mechanism when the absorber is constituted from the pulp fiber and the superabsorbent polymer, although the superabsorbent polymer exhibits by itself an astounding absorption power, there are problems such as that the water-absorbing power cannot be exhibited if it is not wetted to some extent and that the absorption speed is slow; therefore, the pulp fiber that has an absorption speed remarkably larger than that of the superabsorbent polymer absorbs instantaneously. And, belatedly to this, an absorption form is taken in which the urine retained between gaps of the pulp fibers moves to the superabsorbent polymer side.

Accordingly, in the present invention, in order to satisfy with good balance all of rapid absorption performance immediately after the urination, prevention performance against rebounding to the surface after absorption of the urine by the absorber, and residual liquid reduction performance in the front-surface sheet, the absorber is set with a basis weight of the pulp fiber of 75 to 300 g/m$^2$, a basis weight of the superabsorbent polymer is set to 85 to 185 g/m$^2$, and a ratio of the pulp fiber and the superabsorbent polymer is set to pulp fiber:superabsorbent polymer=70 to 30% by weight:30 to 70% by weight.

When the blending ratio of the pulp fiber is larger than 70% by weight, and the blending ratio of the superabsorbent polymer is smaller than 30% by weight, since the content ratio of the pulp fiber becomes higher, the liquid retentiveness of the absorber is low, and there is concern that the rebounding to the front-surface sheet may occur after the urination. On the other hand, when the blending ratio of the pulp fiber is smaller than 30% by weight and the blending ratio of the superabsorbent polymer is larger than 70% by weight, since the content ratio of the superabsorbent polymer becomes higher, an initial absorption speed immediately after the urination is slow, and there is concern that residual liquid on the front-surface sheet may occur immediately after the urination.

As the present invention according to Claim 2, the absorbent article according to Claim 1 is provided, in which the front-surface sheet is made of non-degreased cotton fiber.

According to the invention described in Claim 2, since the non-degreased cotton fiber is used in the front-surface sheet, due to a natural fat of cotton wax adhered to a surface of the cotton fiber, it becomes even more difficult for the front-surface sheet to absorb the body fluid.

As the present invention according to Claim 3, the absorbent article according to any one of Claims 1 and 2 is provided, in which glyceryl stearate is used as the water repellent agent, and a coating amount of the water repellent agent is 0.05 to 0.30 parts by weight relative to 100 parts by weight of the pulp fiber.

According to the invention described in Claim 3, when glyceryl stearate is used as the water repellent agent and the coating amount thereof is set to 0.05 to 0.30 parts by weight relative to 100 parts by weight of the pulp fiber, the urine is not absorbed by the cotton fiber of the front-surface sheet and tends to flow to an absorber side.

Effect of the Invention

As described in detail above, according to the present invention, in the absorbent article that uses cotton fiber in the front-surface sheet, when the absorber is provided in which predetermined amounts of the pulp and the polymer are blended, an absorbent article can be provided in which the rebounding is prevented, the absorption speed is improved, and the diffusion range of the urine in the front-surface sheet is reduced.

BRIEF DESCRIPTION OF THE DRAWINGS

FIG. 1 is a partially broken development view of an incontinence pad 1 according to the present invention.

FIG. 2 is a view from an arrow direction along II-II lines in FIG. 1.

FIG. 3 is a view from an arrow direction along lines in FIG. 1.

FIG. 4 is an enlarged plan view of a front-surface sheet 3.

FIG. 5 is a development view showing a coating pattern of a water repellent agent on a surface of a front-surface sheet 3.

MODES FOR CARRYING OUT THE INVENTION

In what follows, an embodiment of the present invention will be described in detail with reference to the drawings. The present invention is an incontinence pad 1 of medium or larger volume suitable for a total volume of urine that is 20 cc or larger, and is particularly suitable for absorbing urine that is instantaneously excreted when force is applied to an abdominal part such as when sneezing, coughing, or when holding a heavy object.

One Example of Basic Structure of Incontinence Pad

An incontinence pad 1 according to the present invention is constituted mainly of, as shown in FIGS. 1 to 3: an impermeable back-surface sheet 2 made of a polyethylene sheet; a front-surface sheet 3 that forms a skin-contact surface and allows rapid permeation of urine or the like; an absorber 4 interposed between both sheets 2 and 3 and made of cotton pulp or synthetic pulp; and a pair of right and left three-dimensional gathers BS and BS provided by protruding with a substantial lateral edge part of the absorber 4 as a rise-up base edge on a skin side within a predetermined interval in the front-back direction so as to contain at least a urinating hole H of a wearer, and in the surrounding of the absorber 4, at upper and lower end edge parts thereof, outer edge parts of the impermeable back-surface sheet 2 and the front-surface sheet 3 are joined by an adhesive such as a hot melt or by adhering means such as a heat seal, furthermore, at both lateral edge parts thereof, the impermeable back-surface sheet 2 that extends further on the lateral side than the absorber 4 and a side non-woven fabric 7 that forms the three-dimensional gather BS are joined by an adhesive such as a hot melt or by adhering means such as a heat seal. In an illustrated example, the absorber 4 is formed into a single-layer structure but may be formed into a multi-layered structure that forms a center high part, and also may be formed into a multi-layered structure in which absorbers having the same magnitude and shape are stacked.

In the impermeable back-surface sheet 2, although a sheet material having at least a water-blocking property such as polyethylene is used, in recent years, from the viewpoint of preventing a moist feeling, a material having moisture permeability tends to be used. As the water-blocking and moisture permeable sheet material, a microporous sheet that is obtained by molding a sheet by melting and kneading an inorganic filler in an olefin-based resin such as polyethylene or polypropylene, followed by stretching in one or biaxial direction is suitably used. On a unused surface side (outside surface) of the impermeable back-surface sheet 2, one or a plurality of stripes of adhesive layers (not shown in the drawing) are formed, the incontinence pad 1 is fixed to an underwear when wearing on the body. As the impermeable back-surface sheet 2, a polylaminated nonwoven fabric obtained by laminating a plastic film and a nonwoven fabric may be used.

In the illustrated example, the front-surface sheet 3 is formed to an extent whereby the front-surface sheet 3 has a width slightly larger than a width of the absorber 4 and covers only the absorber 4, and the outside in the width direction of the front-surface sheet 3 is covered with the side nonwoven fabric 7 (a member separate from the front-surface sheet 3) that extends from surfaces of both side parts of the front-surface sheet 3. A part on a center side in the width direction of the side nonwoven fabric 7 forms a three-dimensional gather BS. As the side nonwoven fabric 7, in response to objectives such as prevention of permeation of urine or enhancement of feeling on the skin, a nonwoven fabric material to which appropriate water repelling treatment or hydrophilic treatment is applied can be used. As such side nonwoven fabric 7, one formed according to a processing method with a natural fiber, a synthetic fiber or a recycled fiber as a raw material can be used. However, preferably, in order to eliminate a stiff feeling and to prevent a moist feeling, a nonwoven fabric given an aeration property by suppressing basis weight may be used. Specifically, a nonwoven fabric produced by setting the basis weight of 15 to 23 $g/m^2$ is desirably used, and in order to securely prevent permeation of the body fluid, a nonwoven fabric to which water repelling treatment is applied by coating with a water repelling agent based on silicon or paraffin may be suitably used.

As shown in FIGS. 2 and 3, the side nonwoven fabric 7 is adhered at an outside portion with respect to an intermediate portion in a width direction by an adhesive such as a hot melt over a range from an inside position of the absorber 4 to an outer periphery of impermeable back-surface sheet 2 slightly exceeding an absorber side edge.

On the other hand, an inner side portion of the side nonwoven fabric 7 is folded substantially into two fold and in the inside of the two-folded sheet, one or a plurality of thread-like elastic stretchable members, two thread-like elastic stretchable members 8 and 8 in the illustrated example, in which both ends or appropriate positions at in the longitudinal direction are fixed in the intermediate part in the height direction, the thread-like elastic stretchable members being provided in a state where both ends or an appropriate position in the longitudinal direction are fixed in the middle portion in the height direction of the two-folded sheet. This double-folded part is, in the front and back end parts, fixed on the front-surface sheet 3 side in a folded state as shown in FIG. 3.

(Front-Surface Sheet)

The front-surface sheet 3 forms a skin-contact surface that is a part that covers a skin side of the absorber 4 and is constituted of a spunlace nonwoven fabric made of 100% cotton fiber by weight. The spunlace nonwoven fabric has advantageous points such as that it does not use the adhesive agent and that it has flexibility.

The nonwoven fabric of the front-surface sheet 3 is used with the cotton fiber alone and does not contain a synthetic fiber. As the cotton fiber, although all cotton fibers such as raw cotton of cotton, refined/bleached cotton fiber or dyed cotton fiber after refining/bleaching, refined/bleached and degreased cotton fiber, further, recovered wool obtained by fibrillating one that was formed into thread or cloth or the like can be used, in particular, non-degreased cotton provided with a slight water repellency even in a state of fiber due to natural fat of cotton wax adhered to a surface of the cotton fiber is preferably used.

The basis weight of the front-surface sheet 3 is set at 20 to 40 g/m$^2$, preferably at 27 to 34 g/m$^2$, and more preferably at 29 to 32 g/m$^2$, and a thickness is set at 0.25 to 0.50 mm, and preferably at 0.3 to 0.4 mm. The basis weight is calculated by measuring a weight of 10 sheets sized 5 cm×30 cm with an electronic balance followed by converting into units per one square meter. Furthermore, the thickness is obtained according to JIS-L 1906.

As shown in FIG. 4, the front-surface sheet 3 is provided with many front-face/back-face penetrating openings 10, 10 . . . to enhance the permeability. Specifically, the openings 10 can be formed by making a fiber material be carried on a mesh-like support in a stream interlacing process during manufacture of the spunlace. In this case, by changing a condition of a mesh used, an individual opening size and an aperture ratio can be adjusted. Of course, the openings may be formed by punching the nonwoven fabric after manufacture. The openings 10 may be provided over an entire front-surface sheet but may be formed on a region containing at least a part H corresponding to a urinating hole. The openings 10 are preferably provided in a region that contains the part H corresponding to the urinating hole, that is 15% or more of an absorber length in a product length direction, and that is 50% or more of an absorber width in a product width direction, and, more preferably, in a region that contains the part H corresponding to the urinating hole, that is 50% or more of an absorber length in a product length direction, and that is 70% or more of an absorber width in a product width direction. When a formation region of the openings is shorter than 15% of an absorber length in a product length direction, and shorter than 50% of an absorber width in a product width direction, a situation where the incontinence region cannot be covered occurs, the urine remains on the front-surface sheet 3 to cause a sticky feeling, and a skin trouble such as itchiness or irritation tends to occur during wearing.

Since as the front-surface sheet 3, one that includes the spunlace nonwoven fabric that is made of 100% cotton fiber by weight, is coated with the water repellent agent and has many front-face/back-face penetrating openings in the region containing the part H corresponding to the urinating hole is used, a soft feeling on the skin can be obtained, and skin trouble during wearing such as itchiness or irritation is made to occur less easily even when wearing for a long time. The residual liquid on a surface that becomes a problem at this time may be sufficiently improved by coating with the water repellent agent. Furthermore, since front-face/back-face penetrating openings are provided in a region of the front-surface sheet 3 containing the part H corresponding to the urinating hole, the body fluid permeates speedily through the front-surface sheet via these openings.

As shown in FIG. 4, the openings 10 are formed in a vertically long shape that is long in the longitudinal direction of the incontinence pad 1. Therefore, since the body fluid can more readily permeate through these openings 10 than through circular openings, it becomes easy for the urine to permeate through the front-surface sheet 3 via these openings 10, and water retained in the front-surface sheet 3 is reduced. Furthermore, when the urine permeates through the openings 10, since the liquid passes through while being transformed into a vertically long shape, a diffusion direction of the urine can be controlled to a pad longitudinal direction, diffusion in the lateral direction is suppressed, and it becomes difficult for lateral leakage to occur. Although in the case of the spunlace, it is difficult for the shape of openings to become uniform, a shape of the opening 10 becomes a shape like a substantial rectangle to a truncated long hole shape or an elliptical shape.

As a dimension of the opening 10, a length L1 in the longitudinal direction of the incontinence pad 1 may be set at 1.0 to 4.0 mm and preferably 1.5 to 3.0 mm, and a length L2 in the width direction of the incontinence pad 1 may be set at 0.5 to 1.5 mm and preferably 0.5 to 1.0 mm. When a dimension of the opening 10 is smaller than 0.5 mm, it is difficult for the urine to permeate and it is difficult for a clear opening to be formed due to fluffing of the fiber, and when a maximum dimension of the opening 10 exceeds 4.0 mm, the rebounding of the liquid from the opening 10 and surface exposure of a constituent material of the absorber 4 may be caused. Furthermore, a ratio of L1 and L2 (L1/L2) may be set at 1.2 to 5.0, and preferably 2.0 to 3.0. An area A of the opening 10 may be set at 0.9 to 3.0 mm$^2$ and preferably 0.9 to 2.5 mm$^2$. Furthermore, the aperture ratio may be set at 15 to 45%, preferably 17 to 30% and more preferably 18 to 25%. The dimension of the opening 10 is not necessarily uniform over an entirety but may be formed at an arbitrary dimension as long as it is within the above range.

As shown in FIG. 4, the front-surface sheet 3 has a structure in which many vertical streaks 11, 11 . . . that extend along the longitudinal direction of the incontinence pad 1 and are formed with gaps in the width direction, and many lateral streaks 12, 12 . . . that extend along the width direction of the incontinence pad 1 and connect between adjacent vertical streaks 11, 11 that are formed with a gap in the longitudinal direction are formed by the cotton fiber, and the openings 10 are formed in a part surrounded by the vertical streaks 11 and lateral streaks 12.

A width W1 of the vertical streak 11 may be set at 0.5 to 2.5 mm and preferably 0.8 to 1.3 mm, and a width W2 of the lateral streak 12 may be set at 0.2 to 1.6 mm and preferably 0.3 to 0.7 mm. Furthermore, a ratio of the width W1 and W2 (W1/W2) may be set at 1.2 to 2.0 and preferably 1.5 to 2.0. When the width W1 of the vertical streak 11 is made larger than the width W2 of the lateral streak 12, liquid diffusion in the longitudinal direction of the incontinence pad 1 along the vertical streak 11 tends to occur.

The vertical streak 11 is formed with a fiber amount larger and a density higher than the lateral streak 12. Thereby, only a part of the vertical streaks 11 contact with the skin, and due to reduction of a contact area with the skin, skin trouble during wearing such as itchiness or irritation is made to occur less easily even when wearing for a long time, and at the same time, the sticky feeling after the incontinence is alleviated. Furthermore, when the urine permeates through the front-surface sheet 3, due to a capillary action of the fiber, diffusion in the longitudinal direction of the incontinence pad 1 along the vertical streaks 11 having a relatively high density tends to occur. Still furthermore, since the diffusion directions of the urine that permeates through the openings 10 and the urine that permeates through the front-surface sheet 3 are coincident in the longitudinal direction of the incontinence pad 1, the urine permeates through the vertical streaks 11 of the front-surface sheet 3 so as if being pulled by the urine that permeates through the openings 10. Thus, the residual liquid on the front-surface sheet 3 can be suppressed to as small as possible.

Measurement of the fiber amount can be carried out according to JIS P8207 "Pulps—Test method for classification with screens". Furthermore, measurement of the density can be carried out according JIS P8118 "Paper and board—Determination of thickness, density and specific volume".

The front-surface sheet 3 is externally coated with a water repellent agent. As the water repellent agent, among known ones such as paraffin-based and silicone-based ones, one that is less irritant to a skin can be appropriately selected and used. However, it is more preferable to appropriately select and use a less irritant fat such as glyceryl stearate, stearic acid amide, zinc stearate, calcium stearate, stearic acid diethanol amide, and magnesium stearate. Among these, glyceryl stearate is particularly preferable. When the water repellent agent made of glyceryl stearate is used in the continence pad 1, a coating amount thereof is preferably set at 0.05 to 0.30 parts by weight relative to 100 parts by weight of the fiber (a total coating amount on both sides in the case of double-side coating). A more preferable coating amount is 0.08 to 0.25 parts by weight. When the coating amount of the water repellent agent is less than 0.05 parts by weight, the water repellent effect may be deficient, and when exceeding 0.30 parts by weight, the water repellency is excessively high, result in difficulty for moisture to permeate.

Although the water repellent agent may be coated only on a skin-contact surface or may be coated on both sides of the skin-contact surface and a surface on the absorber 4 side, it is preferable to set a water absorption capacity, obtained from at least a water absorption capacity test described below, at 0.03 g or smaller, preferably at 0.02 g or smaller.

The water absorption capacity of the front-surface sheet 3 was obtained according to the following procedure. (1) A sample of 10 cm square is prepared and a weight thereof is measured (A). (2) Three sheets of filter paper of 10 cm square are stacked with a smooth surface side upward and the test sample is set thereon. (3) On the set sample, 3 ml of tap water at normal temperature is dropped, and is subsequently left for 5 minutes. (4) A weight of the sample left for 5 minutes is measured (B). (5) The water absorption capacity (water retention capacity) of the front-surface sheet 3 is obtained from (B)−(A)=water absorption capacity (g).

In particular, it is preferable that the water absorbency of a surface on the absorber 4 side is higher than the water absorbency of the skin-contact surface in the front-surface sheet 3. Therefore, the water absorbency on the skin contact side (JIS L1907 Byreck method) is 0 mm to 5 mm, preferably 0 mm to 2 mm, and the water absorbency on the absorber 4 side (JIS L1907 Byreck method) is about 0 mm to 10 mm, particularly preferably about 2 mm to 4 mm. Such a difference in the water absorbency can be readily obtained by coating with the water repellent agent only on the skin-contact surface of the front-surface sheet 3, and can also be obtained when the water repellent agent is coated on both sides of the front-surface sheet 3, in this case, the water repellent agent is coated on a surface on the absorber 4 side in a smaller amount than on the skin-contact surface. Even when the water repellent agent is coated only on the skin-contact surface of the front-surface sheet 3, depending on the thickness or the basis weight, a surface on the absorber 4 side becomes water-repellent. Whether the water repellent agent is coated only on one side or on both sides, or how a ratio of coating amounts on both sides is set when coating on both sides, appropriate selection is made such that, in addition to the conditions of the thickness of the front-surface sheet 3, the basis weight, and the conditions of openings, the water permeability and water absorbance can be held in a good balance.

As a coating method of the water repellent agent, well-known methods such as a transfer method, a misting method, a brushing method, a soaking method, or a dipping method can be appropriately used. When a difference of water absorbance is provided between both sides of the sheet, a coating method by transfer can be preferably used.

The water repellent agent is preferably coated over an entire surface from the viewpoint of production efficiency but may be coated only on a part that receives the excreted liquid. For example, as shown in FIG. 5(A), a water repellent agent coating part 40 may be provided excluding both side parts in the width direction. Furthermore, as shown in FIG. 5(B), the water repellent coating part 40 may be provided only on a part central in the width direction and intermediate in the front-back direction.

(Absorber 4)

The absorber 4 can absorb and retain the urine, and an absorber 4 may be used in which the particulate superabsorbent polymer is dispersed and mixed in the fluffy pulp fiber The absorber 4 is made of only the pulp fiber and the superabsorbent polymer and does not contain the synthetic fiber.

As the pulp fiber, ones made of cellulose fibers such as chemical pulp obtained from timber or molten pulp, and artificial cellulose fibers such as rayon and acetate can be used; and ones made of softwood pulp having a fiber length longer than hardwood pulp are suitably used from the viewpoint of function and price.

The basis weight of the pulp fiber is set at 75 to 300 g/m$^2$, and preferably at 155 to 270 g/m$^2$, and the basis weight of the superabsorbent polymer is set at 85 to 185 g/m$^2$, and preferably at 100 to 165 g/m$^2$.

As the superabsorbent polymer, for example, one obtained by partially crosslinking a water-swelling polymer such as a crosslinked polyacrylate, a self-crosslinked polyacrylate, a saponified acrylic acid ester-vinyl acetate copolymer crosslinked product, an isobutylene/maleic anhydride copolymer crosslinked product, a crosslinked polysulfonate, polyethylene oxide, and polyacryl amide can be used. Among these, acrylic acid-based or acrylate-based polymers having excellent water absorption capacity and water absorption speed are preferable. In the superabsorbent polymer having the water absorbance, the absorption rate (water absorption power) and absorption speed may be adjusted by adjusting a crosslinking density and a crosslinking density gradient in the production process of the superabsorbent polymer.

A ratio of the pulp fiber and superabsorbent polymer is set at pulp fiber:superabsorbent polymer=70 to 30% by weight: 30 to 70% by weight, preferably at 62 to 45% by weight:38 to 55% by weight, and more preferably at 60 to 50% by weight:40 to 50% by weight.

In the present incontinence pad 1, since an absorber in which a pulp fiber and a superabsorbent polymer each is constituted at a predetermined basis weight and the pulp fiber and the superabsorbent polymer each is constituted at a predetermined weight ratio is used, even when the urine is instantaneously excreted, the pulp fiber having rapid absorption speed rapidly absorbs the urine immediately after the urination, thereafter, the urine absorbed by the pulp fiber is gradually absorbed by the superabsorbent polymer and retained therein, wherein the rebounding to the surface can be prevented.

By contrast, when the pulp fiber is contained in more than 70% by weight and the superabsorbent polymer is contained in less than 30% by weight, since the content ratio of the pulp fiber becomes higher, the water retentiveness of the absorber 4 is low, and the rebounding to the front-surface sheet 3 after urination tends to occur. On the other hand, when the pulp fiber is contained in less than 30% by weight and the superabsorbent polymer is contained in more than 70% by weight, since the content ratio of the superabsorbent polymer becomes high, an initial absorption speed immediately after the urination is slow, the transfer of the urine from the front-surface sheet 3 to the absorber 4 does not proceed smoothly, and the presence of residual liquid tends to occur on the front-surface sheet 3 immediately after the urination.

Furthermore, since the urine is securely absorbed and retained in the absorber from immediately after the urination and the residual liquid does not occur in the front-surface sheet, a diffusion range of the urine on the front-surface sheet can be suppressed from expanding.

The absorber 4 is desirably surrounded by a wrapping sheet 5 such as crepe paper for shape retention and polymer powder retention.

(Intermediate Sheet)

The front-surface sheet 3 of the incontinence pad 1 according to the present invention includes many openings 10. In order to prevent the pulp, polymer, adhesive or the like that constitute the absorber 4 from being exposed from the openings 10, an intermediate sheet 6 is preferably provided between the front-surface sheet 3 and the absorber 4. The intermediate sheet 6 also has a function of preventing the rebounding from the absorber 4 and of making a soft feeling on the skin soft due to a cushion-like effect while wearing.

The intermediate sheet 6 illustrated in the example drawing is formed into a single layer structure but may be formed into a two-layer structure by folding the intermediate sheet 6 into a tube shape. The intermediate sheet 6 may be provided over an entire skin-contact surface or may be provided only on a center in the width direction and on the intermediate part in the front-back direction (in particular, on a groin part).

A raw material of the intermediate sheet 6 may be any that has permeability but is particularly preferably one having hydrophilicity. By combining the hydrophilic intermediate sheet 6 such as this with a water-repelling holed front-surface sheet 3 of the present invention, the permeability and back flow prevention performance of the front-surface sheet 3 are remarkably improved. As such a hydrophilic raw material, fibers having hydrophilicity in the raw material itself are used by using recycled fiber such as rayon or cupra, or natural fiber such as cotton or the like; alternatively, fibers may be used in which synthetic fibers such as olefin-based, including polyethylene, polypropylene and the like, polyester-based, polyamide-based, or composite fibers thereof, copolymers or blend bodies are surface-treated with a hydrophilizing agent to impart hydrophilicity. Preferably, a fiber obtained by mixing polyethylene and polypropylene is used. As the fiber that constitutes the nonwoven fabric, any one of a long fiber, a short fiber, or a mixture thereof can be used. It is better to set the fineness at about 3.0 to 7.0 dtex, and preferably at about 4 to 6 dtex. As the intermediate sheet 6, any of known portable-use nonwoven fabric such as an air through nonwoven fabric, an air laid nonwoven fabric, a spun-bond nonwoven fabric or the like can be used, but the air through nonwoven fabric that does not degrade the permeability is preferably used.

Furthermore, in the case of the incontinence pad, as described above, in many cases, it is continuously used until two instances of incontinences. Therefore, it is more preferable to use not a simple hydrophilic nonwoven fabric but a strongly hydrophilic or durable hydrophilic nonwoven fabric obtained by spraying a strongly hydrophilic agent and/or a durable hydrophilic agent on the nonwoven fabric. The basis weight of the strongly hydrophilic agent or a durable hydrophilic agent is set at 10 to 40 g/m$^2$, and preferably at about 25 g/m$^2$. The basis weight of the intermediate sheet 6 is preferably 20 to 30 g/m$^2$.

In the front-surface sheet 3, in order to prevent the residual liquid of the urine and to make a skin trouble such as itchiness or irritation less easy to occur during wearing, in a region including a part H corresponding to an excreting hole, many front-face/back-face penetrating openings 10 are formed. Therefore, the intermediate sheet 6 is arranged in a size that covers at least an entire surface of the opening formation region (preferably, when the openings are formed in a region which includes the part H corresponding to the excreting hole, which is 15% or more of the absorber body length in the product length direction and which is 50% or more of the absorber width in the product width direction, a size that is 9% or more of the size of the absorber 4 and that covers an entire surface of the opening formation region is desirable.).

The front-surface sheet 3 is desirably adhered by a hot-melt adhesive because heat embossing cannot be adopted. The kind of the hot-melt adhesive is not limited but an SBS (styrene-butadiene-styrene block copolymer)-based hot-melt adhesive is desirable.

EXAMPLES (Test 1)

The present invention is an incontinence pad that uses a spunlace nonwoven fabric made of 100% cotton fiber subjected to water repelling treatment and has many openings formed therein as a front-surface sheet. First, a functional evaluation of effects provided by a constitution of the present invention will be performed to verify the effects. As the evaluation, two kinds of a laboratory evaluation (test room evaluation) and an actual use evaluation were performed. Laboratory evaluation: 10 cc of urine was injected in the region of a urination hole, after 5 minutes, by manually touching a surface of an absorbent article, a three-grade evaluation of good: ○, fair: Δ and poor: x was performed. Furthermore, actual use evaluation: 20 women monitor testers wore and evaluated each product according to a three-grade evaluation of: good: ○, fair: Δ and poor: x.

In the test, an incontinence pad produced with a holed nonwoven fabric made of 100% non-degreased or degreased cotton fiber by weight (basis weight: 30 $g/m^2$, thickness: 0.35 mm) and coated with a water repellent agent as a front-surface sheet, and an absorber made of a pulp fiber having the basis weight of 155 $g/m^2$ and the superabsorbent polymer having the basis weight of 145 $g/m^2$ having pulp fiber:superabsorbent polymer=51% by weight: 49% by weight was used as base (Examples 1 and 2); Comparative Example 1 was a case where degreased cotton was used, the water repellent treatment was not applied, and openings were formed; Comparative Example 2 was a case where degreased cotton was used, the water repellent treatment was not applied, and the openings were not formed; Comparative Example 3 was a case where non-degreased cotton was used, the water repellent treatment was applied, and the openings were not formed; and Comparative Example 4 was a case where degreased cotton was used, the water repellent treatment was applied, and the openings were not formed.

A second sheet (intermediate sheet) was used in common, and a PE/PP, 5.6 dtex, air through nonwoven fabric 25 $g/m^2$ (durably hydrophilic) was used.

Test results are shown in Table 1.

TABLE 1

| Item | Example 1 | Example 2 | Comparative Example 1 | Comparative Example 2 | Comparative Example 3 | Comparative Example 4 |
|---|---|---|---|---|---|---|
| Water repellent treatment | Yes | Yes | No | No | Yes | Yes |
| Openings | Yes | Yes | Yes | No | No | No |
| Degreased or non-degreased | Non-degreased | Degreased | Degreased | Degreased | Non-degreased | Degreased |
| (Laboratory evaluation) | | | | | | |
| Dry feeling after absorption (Actual use evaluation) | ○ | ○ | | X | X | X |
| Dry feeling of front-surface sheet before urination | ○ | ○ | ○ | ○ | ○ | ○ |
| Dry feeling immediately after urination | ○ | ○ | X | X | X | X |
| Dry feeling when time passed after urination | ○ | ○ | X | X | X | X |

(Test 2)

In test 2, absorbers in which the amount of pulp fiber, the amount of polymer and the ratio thereof are varied respectively are subjected to functional evaluation to verify the effects. As the evaluation, two kinds of a laboratory evaluation (test room evaluation) and an actual use evaluation were performed. Laboratory evaluation: 10 cc of urine was injected in the region of a urination hole, after 5 minutes, by manually touching a surface of an absorbent article, a three-grade evaluation of good: ○, fair: Δ and poor: x was performed. Furthermore, actual use evaluation: 20 women monitor testers wore and evaluated each product according to a three-grade evaluation of good: ○, fair: Δ and poor: x.

In the test, an incontinence pad that uses a holed nonwoven fabric made of 100% non-degreased cotton fiber by weight (basis weight: 30 g/m$^2$, thickness: 0.35 mm) and coated with a water repellent agent as a front-surface sheet was used.

A second sheet (intermediate sheet) was commonly used, and a PE/PP, 5.6 dtex, air through nonwoven fabric 25 g/m$^2$ (durably hydrophilic) was used.

Test results are shown in Table 2 and Table 3.

TABLE 2

| Item | Example 3 | Example 4 | Example 5 | Example 6 | Example 7 | Example 8 |
|---|---|---|---|---|---|---|
| Pulp basis weight (g/m$^2$) | 170 | 155 | 170 | 209 | 216 | 264 |
| Polymer basis weight (g/m$^2$) | 110 | 145 | 130 | 154 | 163 | 134 |
| Pulp amount ratio (%) | 61 | 51 | 57 | 58 | 57 | 62 |
| Polymer amount ratio (%) | 39 | 49 | 43 | 42 | 43 | 38 |
| (Laboratory evaluation) | | | | | | |
| Dry feeling after absorption | ○ | ○ | ○ | ○ | ○ | ○ |
| (Actual use evaluation) | | | | | | |
| Dry feeling of front-surface sheet before urination | ○ | ○ | ○ | ○ | ○ | ○ |
| Dry feeling immediately after urination | ○ | ○ | ○ | ○ | ○ | ○ |
| Dry feeling when time passed after urination | ○ | ○ | ○ | ○ | ○ | ○ |

TABLE 3

| Item | Example 9 | Example 10 | Example 11 | Example 12 | Comparative Example 5 | Comparative Example 6 | Comparative Example 7 | Comparative Example 8 |
|---|---|---|---|---|---|---|---|---|
| Pulp basis weight (g/m$^2$) | 76 | 79 | 207 | 251 | 49 | 51 | 244 | 273 |
| Polymer basis weight (g/m$^2$) | 178 | 185 | 87 | 107 | 196 | 203 | 60 | 69 |
| Pulp amount ratio (%) | 30 | 30 | 70 | 70 | 20 | 20 | 80 | 80 |
| Polymer amount ratio (%) | 70 | 70 | 30 | 30 | 80 | 80 | 20 | 20 |
| (Laboratory evaluation) | | | | | | | | |
| Dry feeling after absorption | ○ | ○ | ○ | ○ | X | X | X | X |
| (Actual use evaluation) | | | | | | | | |
| Dry feeling of front-surface sheet before urination | ○ | ○ | ○ | ○ | ○ | ○ | ○ | ○ |
| Dry feeling immediately after urination | ○ | ○ | ○ | ○ | X | X | X | X |
| Dry feeling when time passed after urination | ○ | ○ | ○ | ○ | X | X | X | X |

(Test 3)

In test 3, cases in which each of an area per one opening, an opening dimension ratio, a formation region of opening (vertical/horizontal), and an opening rate (%) of the front-surface sheet was varied were subjected to a functional evaluation to verify the effects. As the evaluation, two kinds of a laboratory evaluation (test room evaluation) and an actual use evaluation were performed. Laboratory evaluation: 10 cc of urine was injected in the region of a urination hole, after 5 minutes, by manually touching a surface of an absorbent article, a four-grade evaluation of excellent: ⊚, good: ○, fair: Δ and poor: x was performed. Furthermore, actual use evaluation: 20 women monitor testers wore and evaluated each product according to a four-grade evaluation of excellent: ⊚, good: ○, fair: Δ and poor: x.

In the test, an incontinence pad produced with a holed nonwoven fabric made of 100% by weight of non-degreased cotton fiber (basis weight: 30 g/m$^2$, thickness: 0.35 mm) and coated with a water repellent agent as a front-surface sheet, and an absorber made of a pulp fiber having the basis weight of 155 g/m$^2$, and the superabsorbent polymer having the basis weight of 145 g/m$^2$ having pulp fiber:superabsorbent polymer=51% by weight:49% by weight was used as base, and tests of Examples 13 to 32 were carried out.

As a second sheet (intermediate sheet), a PE/PP, 5.6 dtex, air through nonwoven fabric 25 g/m$^2$ (durable hydrophilic treatment) was used in common, and the tests were carried out by varying the size of the sheets.

Test results are shown in Table 4.

TABLE 4

| Item | | Example 13 | Example 14 | Example 15 | Example 16 | Example 17 | Example 18 | Example 19 | Example 20 | Example 21 | Example 22 |
|---|---|---|---|---|---|---|---|---|---|---|---|
| Product length (mm) | | 210 | 210 | 210 | 210 | 210 | 210 | 210 | 210 | 210 | 210 |
| Product width (mm) | | 90 | 90 | 90 | 90 | 90 | 90 | 90 | 90 | 90 | 90 |
| Absorber length (mm) | | 170 | 170 | 170 | 170 | 170 | 170 | 170 | 170 | 170 | 170 |
| Absorber width (mm) | | 65 | 65 | 65 | 65 | 65 | 65 | 65 | 65 | 65 | 65 |
| (1) | (2) | 2.2 | 2.2 | 2.2 | 2.2 | 2.2 | 1.0 | 1.0 | 3.0 | 3.0 | 0.5 |
| | (3) | 2.0 | 2.0 | 2.0 | 2.0 | 2.0 | 1.6 | 1.6 | 1.6 | 1.6 | 1.2 |
| | (4) | 170 | 170 | 170 | 170 | 170 | 170 | 170 | 170 | 170 | 170 |
| | (5) | 100 | 100 | 100 | 100 | 100 | 100 | 100 | 100 | 100 | 100 |
| | (6) | 65 | 65 | 65 | 65 | 65 | 65 | 65 | 65 | 65 | 65 |
| | (7) | 100 | 100 | 100 | 100 | 100 | 100 | 100 | 100 | 100 | 100 |
| | (8) | 15 | 22 | 45 | 10 | 50 | 15 | 45 | 15 | 45 | 15 |
| (9) | (10) | 170 | 170 | 170 | 170 | 170 | 170 | 170 | 170 | 170 | 170 |
| | (11) | 65 | 65 | 65 | 65 | 65 | 65 | 65 | 65 | 65 | 65 |
| | (12) | 100 | 100 | 100 | 100 | 100 | 100 | 100 | 100 | 100 | 100 |
| (13) | | | | | | | | | | | |
| (14) | | ⊚ | ⊚ | ⊚ | ○ | ○ | ⊚ | ⊚ | ⊚ | ⊚ | ○ |
| (15) | | | | | | | | | | | |
| (16) | | ⊚ | ⊚ | ⊚ | ⊚ | ⊚ | ⊚ | ⊚ | ⊚ | ⊚ | ⊚ |
| (17) | | ⊚ | ⊚ | ⊚ | ○ | ○ | ⊚ | ⊚ | ⊚ | ⊚ | ○ |
| (18) | | ⊚ | ⊚ | ⊚ | ○ | ○ | ⊚ | ⊚ | ⊚ | ⊚ | ○ |

| Item | | Example 23 | Example 24 | Example 25 | Example 26 | Example 27 | Example 28 | Example 29 | Example 30 | Example 31 | Example 32 |
|---|---|---|---|---|---|---|---|---|---|---|---|
| Product length (mm) | | 210 | 210 | 210 | 210 | 210 | 210 | 210 | 210 | 210 | 210 |
| Product width (mm) | | 90 | 90 | 90 | 90 | 90 | 90 | 90 | 90 | 90 | 90 |
| Absorber length (mm) | | 170 | 170 | 170 | 170 | 170 | 170 | 170 | 170 | 170 | 170 |
| Absorber width (mm) | | 65 | 65 | 65 | 65 | 65 | 65 | 65 | 65 | 65 | 65 |
| (1) | (2) | 0.5 | 0.5 | 4.0 | 4.0 | 2.2 | 2.2 | 2.2 | 2.2 | 2.2 | 2.2 |
| | (3) | 1.2 | 1.2 | 2.0 | 2.0 | 2.0 | 2.0 | 2.0 | 2.0 | 2.0 | 2.0 |
| | (4) | 120 | 120 | 170 | 120 | 85 | 85 | 85 | 85 | 26 | 17 |
| | (5) | 71 | 71 | 100 | 71 | 50 | 50 | 50 | 50 | 15 | 10 |
| | (6) | 52 | 52 | 65 | 52 | 46 | 46 | 46 | 46 | 33 | 30 |
| | (7) | 80 | 80 | 100 | 80 | 71 | 71 | 71 | 71 | 51 | 46 |
| | (8) | 45 | 45 | 15 | 45 | 15 | 22 | 22 | 45 | 15 | 15 |
| (9) | (10) | 125 | 170 | 170 | 125 | 90 | 90 | 170 | 90 | 28 | 170 |

TABLE 4-continued

| (11) | 57 | 65 | 65 | 57 | 50 | 50 | 65 | 50 | 36 | 65 |
|---|---|---|---|---|---|---|---|---|---|---|
| (12) | 64 | 100 | 100 | 64 | 41 | 41 | 100 | 41 | 9 | 100 |
| (13) | | | | | | | | | | |
| (14) | ○ | ○ | ○ | ○ | ◎ | ◎ | ◎ | ◎ | ◎ | ○ |
| (15) | | | | | | | | | | |
| (16) | ◎ | ◎ | ◎ | ◎ | ◎ | ◎ | ◎ | ◎ | ◎ | ◎ |
| (17) | ○ | ○ | ○ | ○ | ◎ | ◎ | ◎ | ◎ | ◎ | ○ |
| (18) | ○ | ○ | ○ | ○ | ◎ | ◎ | ◎ | ◎ | ◎ | ○ |

(1) Dimensional data of openings
(2) Area (mm$^2$) per one opening
(3) Dimensional ratio of opening (length/breadth)
(4) Dimension (mm) of an opening region in the product length direction
(5) Ratio (%) of the opening region to an absorber length (in the product length direction including excreting hole)
(6) Dimension (mm) of the opening region in the product length direction
(7) Ratio (%) of the opening region to an absorber width (in a width direction including excreting hole)
(8) Hole ratio*$^1$
(9) Intermediate sheet
(10) Length (mm) of the intermediate sheet in the product direction
(11) Length (mm) of the intermediate sheet in the product width direction
(12) Size of the intermediate sheet*$^2$
(13) (Laboratory evaluation)
(14) Dry feeling after absorption
(15) (Actual use evaluation)
(16) Dry feeling of a front sheet before urination
(17) Dry feeling immediately after urination
(18) Dry feeling when time passed after urination
*$^1$Opening ratio is a ratio (%) of a total area of the openings to a total area of an opening formation region.
*$^2$Size of the intermediate sheet is represented by a ratio (%) to an absorber area under the condition of covering an entire surface of the opening formation region.

EXPLANATION OF REFERENCE NUMERALS

1/INCONTINENCE PAD
2/IMPERMEABLE BACK-SURFACE SHEET
3/FRONT-SURFACE SHEET
4/ABSORBER
5/WRAPPING SHEET
6/INTERMEDIATE SHEET
7/SIDE NONWOVEN FABRIC
8/THREAD-LIKE ELASTIC STRETCHABLE MEMBER
10/OPENINGS
11/VERTICAL STREAK
12/LATERAL STREAK

The invention claimed is:

1. An incontinence absorbent article having an absorber interposed between a front-surface sheet and a back-surface sheet characterized in that:
the incontinence absorbent article is an incontinence pad having a medium or larger volume that absorbs 20 cc or a larger volume of urine;
the front-surface sheet is a spunlace nonwoven fabric made of 100% by weight of cotton fiber, is coated with a water repellent agent and has many front-face/back-face penetrating openings in a region containing a part corresponding to an excreting hole;
the front-surface sheet has a structure in which many vertical streaks that extend along the longitudinal direction of the incontinence absorbent article and are formed with gaps in the width direction and many lateral streaks that extend along the width direction of the incontinence absorbent article and connect between adjacent vertical streaks that are formed with a gap in the longitudinal direction are formed by the cotton fiber; the openings are formed in a part surrounded by the vertical streaks and lateral streaks; a width W1 of each of the vertical streaks is set at 0.5 to 2.5 mm, a width W2 of each of the lateral streaks is set at 0.2 to 1.6 mm, and a ratio of the width W1 to W2 (W1/W2) is set at 1.2 to 2.0;
the openings are formed in a vertically long shape that is long in the longitudinal direction of the incontinence absorbent article and each of the openings has a dimension in which a length L1 in the longitudinal direction of the incontinence absorbent article is set at 1.0 to 4.0 mm, a length L2 in the width direction of the absorber article is set at 0.5 to 1.5 mm, and a ratio of L1 to L2 (L1/L2) is set at 1.2 to 5.0; an area of each of the openings is set at 0.9 to 3.0 mm2, and an aperture ratio is set at 15 to 45%; and
the absorber is made of a pulp fiber that does not contain synthetic fiber and a superabsorbent polymer, a basis weight of the pulp fiber being 75 to 300 g/m2, a basis weight of the superabsorbent polymer being 85 to 185 g/m2, and a ratio of the pulp fiber and the superabsorbent polymer being pulp fiber:superabsorbent polymer=70 to 30% by weight:30 to 70% by weight.

2. The absorbent article according to claim 1, wherein the front-surface sheet is made of non-degreased cotton fiber.

3. The absorbent article according to claim 1, wherein glyceryl stearate is used as the water repellent agent, a coating amount of the water repellent agent being 0.05 to 0.30 parts by weight relative to 100 parts by weight of pulp fiber.

4. The absorbent article according to claim 2, wherein glyceryl stearate is used as the water repellent agent, a coating amount of the water repellent agent being 0.05 to 0.30 parts by weight relative to 100 parts by weight of pulp fiber.

* * * * *